United States Patent [19]
Johansen et al.

[11] Patent Number: 6,046,025
[45] Date of Patent: *Apr. 4, 2000

[54] EXPRESSION OF HETEROLOGOUS PROTEINS IN DROSOPHILA CELLS

[75] Inventors: Hanne Ranch Johansen, Hojbjerg, Denmark; Ariane Adrienne Van Der Straten-Ponthoz, Chicago, Ill.; Martin Rosenberg, Royersford, Pa.

[73] Assignee: SmithKline Beecham Corp., King of Prussia, Pa.

[*] Notice: This patent is subject to a terminal disclaimer.

[21] Appl. No.: 08/433,293

[22] Filed: May 3, 1995

Related U.S. Application Data

[60] Division of application No. 08/098,016, Jul. 27, 1993, Pat. No. 5,681,713, and a continuation-in-part of application No. 07/574,563, Aug. 27, 1990, abandoned, which is a continuation of application No. 07/428,454, Oct. 30, 1989, abandoned, which is a continuation of application No. 07/047,736, May 8, 1987, abandoned, said application No. 08/098,016, is a continuation of application No. 07/681,222, Apr. 5, 1991, abandoned, which is a continuation-in-part of application No. 07/278,386, Dec. 1, 1988, abandoned.

[51] Int. Cl.[7] ............................. C12N 15/10; C12N 5/10; C12N 15/64; C12N 15/67
[52] U.S. Cl. .................... 435/69.1; 435/320.1; 435/348; 536/23.1; 536/24.1; 530/395
[58] Field of Search ................. 435/69.1, 70.3, 435/172.3, 320.1, 348; 514/8; 530/395, 300, 350; 536/24.1, 23.1; 800/DIG. 4; 935/22, 34, 70

[56] References Cited

U.S. PATENT DOCUMENTS

| | | | |
|---|---|---|---|
| 4,399,216 | 8/1983 | Axel et al. | 435/6 |
| 4,431,739 | 2/1984 | Riggs | 435/253 |
| 4,670,388 | 6/1987 | Rubin et al. | 435/172.3 |
| 5,004,686 | 4/1991 | Cohen | 435/69.1 |
| 5,041,370 | 8/1991 | Hamdy et al. | 435/5 |
| 5,041,385 | 8/1991 | Kingsman et al. | 435/320.1 |
| 5,126,433 | 6/1992 | Maddon et al. | 530/395 |
| 5,523,215 | 6/1996 | Cousens et al. | 435/69.1 |
| 5,550,043 | 8/1996 | Johansen et al. | 435/172.3 |
| 5,681,713 | 10/1997 | Johansen et al. | 435/69.1 |
| 5,705,359 | 1/1998 | Johansen et al. | 435/69.1 |

FOREIGN PATENT DOCUMENTS

| | | |
|---|---|---|
| 117059 | 8/1984 | European Pat. Off. . |
| 211260 | 2/1987 | European Pat. Off. . |
| 248647 | 12/1987 | European Pat. Off. . |
| 265785 | 5/1988 | European Pat. Off. . |
| 272858 | 6/1988 | European Pat. Off. . |
| 093619 | 11/1998 | European Pat. Off. . |
| 2181435 | 4/1987 | United Kingdom . |
| WO87/06260 | 10/1987 | WIPO . |

OTHER PUBLICATIONS

J. Sinclair et al., "Regulated Expression of a Drosophila melanogaster Heat Shock Locus After Stable Integration in a Drosophila hydei Cell Line," *Mol. and Cell. Biol.*, vol. 5, No. 11, pp. 3208–3213, Nov. 1985.

H. Johansen et al, "Regulated Expression at High Copy Number Allows Production of a Growth–Inhibitory Oncogene Product in Drosophila Schneider Cells", *Genes & Development*, 3:882–889 (1989).

J. Culp et al, "Regulated Expression Allows High Level Production and Secretion of HIV–1 gp120 Envelope Glycoprotein in Drosophila Schneider Cells", *Biotechnology*, 9:173–177 (Feb., 1991).

M. Ivey–Hoyle, "Recombinant Gene Expression in Cultured Drosophila Melanogaster Cells", *Current Opinion in Biotechnology*, 2:704–707 (1991)

A. van der Straten et al, "Introduction and Constitutive Expression of Gene Products in Cultured Drosophila Cells Using Hygromycin B Selection", *Methods in Molecular and Cellular Biology*, 1(1):1–8 (1989).

T. Bunch et al, "Characterization and Use of the Drosophila Metallothionein Promoter in Cultured Drosophila Melanogaster Cells", *Nucleic Acids Research*, 16(3):1043–1061 (1988).

M. Allday et al, Efficient Expression of an Epstein–Barr Nuclear Antigen in Drosophila Cells Transfected with Epstein–Barr Virus DNA, *EMBO Journal*, 4:2955–2959 (1985).

I. Schneider, "Cell Lines Derived from Late Embryonic Stages of Drosophila Melanogaster", *J. Embryol. Exp. Morph.*, 27(2):353–365 (1972).

D. Lastowski–Perry et al, "Nucleotide Sequence and Expression of a Drosophila Metallothionein", *J. Biol. Chem.*, 260(3):1527–1530 (Feb., 1985).

G. Pavlakis et al, "Regulation of a Metallothionein–Growth Hormone Hybrid Gene in Bovine Papilloma Virus", *Proc. Natl. Acad. Sci. USA*, 80:397–401 (Jan., 1983).

J. Sambrook et al, "Lines of BPV–Transformed Murine Cells that Constitutively Express Influenza Virus Hemmaglutinin", *EMBO J.*, 4(1):91–103 (Jan., 1985).

H. Steller et al, "Regulated Expression of Genes Injected into Early Drosophila Embryos", *EMBO J.*, 3(1):165–173 (1984).

L. Gritz et al, "Plasmid–Encoded Hydromycin B Resistance: the Sequence of Hydromycin B Phosphotransferase Gene and its Expression in *E. coli* and *S. cerevisiae*", *Gene*, 25:179–188 (1983).

B. Sugden et al, "A Vector that Replicates as a Plasmid and can be Efficiently Selected in B–lymphoblasts Transformed by Epstein–Barr Virus", *Mol. Cell. Biol.*, 5(2):410–413 (Feb., 1985).

(List continued on next page.)

*Primary Examiner*—Lila Feisee
*Assistant Examiner*—Claire M. Kaufman
*Attorney, Agent, or Firm*—Kathleen W. Geiger, Esq.; Mary E. Bak, Esq.

[57] ABSTRACT

The present invention provides a novel method for expression of high levels of heterologous proteins in Drosophila cells.

23 Claims, No Drawings

OTHER PUBLICATIONS

M. Bourouis et al, "Vectors Containing a Prokaryotic Dihydrofolate Reductase Gene Transform Drosophila Cells to Methotrexate–Resistance", *EMBO J.*, 2(7):1099–1104 (Jul., 1983).

L. Lasky et al, "Neutralization of the AIDS Retrovirus by Antibodies to a Recombinant Envelope Glycoprotein", *Science*, 223:209–212 (Jul., 1986).

D. Lynn et al, "Production of Recombinant HIV Envelope Protein in Insect Cells and its Potential Use in a Subunit Vaccine", *Mechanisms of Control of Gene Expression*, pp. 359–368, Alan R. Liss, Inc., New York (1988).

D. Pennica et al, "Cloning and Expression of Human Tissue–Type Plasminogen Activator cDNA in *E. coli*", *Nature*, 301:214–221 (Jan., 1983).

R. Karess, "P Element Mediated Germ Line Transformation of Drosophila", *DNA Cloning*, vol. II, Chapter 5, IRL Press, pp. 121–140 (1985).

R. Kaufman et al, "Coamplification and Coexpression of Human Tissue–Type Plasminogen Activator and Murine Dihydrofolate Reductase Sequences in Chinese Hamster Ovary Cells", *Molecular and Cellular Biology*, 5(7):1750–1759 (Jul., 1985).

M. Cochran et al, "Use of Baculovirus Recombinants as a General Method for the Production of Subunit Vaccines", *Vaccines '87*, Cold Spring Harbor Conference on Modern Approaches to New Vaccines, Sep. 9–14, 1986, pp. 384–388 (1986).

J. Rusche et al, "Humoral Immune Response to the Entire Human Immunodeficiency Virus Envelope Glycoprotein Made in Insect Cells", *Proc. Natl. Acad. Sci. USA*, 84:6924–6928 (Oct., 1987).

S. Chakrabarti et al, "Expression of the HTLV–III Envelope Gene by a Recombinant Vaccinia Virus", *Nature*, 320:535–537 (Apr., 1986).

M. Kowalski et al, "Functional Regions of the Envelope Glycoprotein of Human Immunodeficiency Virus Type 1", *Science*, 237:1351–1355 (Sep., 1987).

M. Kieny et al, "AIDS Virus ENV Protein Expressed from a Recombinant Vaccinia Virus", *Biotechnology*, 4:790–795 (Sep., 1986).

S–L. Hu et al, "Expression of AIDS Virus Envelope Gene in Recombinant Vaccinia Viruses", *Nature*, 320:537–540 (Apr., 1986).

D. Knight et al, "Expression of the art/trs Protein of HIV and Study of its Role in Viral Envelope Synthesis", *Science*, 236:837–840 (May, 1987).

S. Pyle et al, "Purification of 120,000 Dalton Envelope Glycoprotein from Culture Fluids of Human Immunodeficiency Virus (HIV)–Infected H9 Cells", *Aids Research and Human Retroviruses*, 3(4):387–400 (1987).

S. Putney et al, "HTLV–III/LAV–Neutralizing Antibodies to an *E. coli*–Produced Fragment of the Virus Envelope", *Science*, 234:1392–1395 (Dec., 1986).

T. Palker et al, "Purification of Envelope Glycoproteins of Human T Cell Lymphotropic Virus Type I (HTLV–I) by Affinity Chromatography", *J. Virol. Meth.*, 18:243–256 (1987).

M. Martin et al, "Expression of Transfected Genes in a Drosophila Cell Line in Transient Assay and Stable Transformation", *J. Insect Physiol.*, 34(7):691–699 (1988).

P. Berman et al, "Expression of Membrane–Associated and Secreted Variants of gp160 of Human Immunodeficiency Virus type 1 in vitro and in Continuous Cell Lines",*J. Virol.*, 62(9):3135–3142 (Sep., 1988).

A. van der Straten et al., Invertebrate and Fish Tissue Culture, Eds., Y. Kuroda, E. Kurstak, and K. Maramorosch (1988), pp. 131–134.

Wurm et al. Inducible overproduction of the mouse c–myc protein in mammalian cells. Proceedings of the National Academy of Sciences, USA. vol. 83, pp. 5414–5418, Aug. 1986.

GenBank Accesssion No. L08752, pUC18 cloning vector. Accessed Feb. 17, 1999, Jan. 1993.

Bond et al. The *Drosophila melanogaster*actin 5C gene uses two transcription initiation sites and three polyadenylation sites to express multiple mRNA species. Molecular and Cellular Biology. vol. 6, No. 6, pp. 2080–2088, Jun. 1986.

Burke et al. An assay for transient gene expression in transfected *Drosophila*cells , using [$^3$H]quanine incorporation. The EMBO Journal. vol. 3, No. 11, pp. 2549–2554, 1984.

Di Nocera et al. Transient expression of genes introduced into cultured cells of *Drosophila*. Proceedings of the National Academy of Sciences, USA. vol. 80, No. 23, pp. 7095–7098, Dec. 1983.

Ivey–Hoyle et al. Rev–dependent expression of human immunodeficiency virus type I gp160 in *Drosophila melanogaster*cells. Molecular and Cellular Biology. vol. 10, No. 12, pp. 6152–6159, Dec. 1990.

McDonald et al. HIV–1 expression is posttranscriptionally repressed in *Drosophila*cells. AIDS Research and Human Retroviruses. vol. 5, No. 1, pp. 79–85, Feb. 1989.

Rio et al. Transformation of Cultured *Drosophila melanogaster*cells with a dominant selectable marker. Molecular and Cellular Biology. vol. 5, No. 8, pp. 1833–1838, Aug. 1985.

Saunders et al. High efficiency expression of transfected genes in a *Drosophila melanogaster*haploid (1182) cell line. Nucleic Acids Research. vol. 17, No. 15, pp. 6205–6216, 1989.

Schweinfest et al. A heat–shock–inducible eukaryotic expression vector. Gene. vol. 72, No. 1, pp. 207–210, Nov. 15, 1988.

EXPRESSION OF HETEROLOGOUS PROTEINS IN DROSOPHILA CELLS

CROSS REFERENCE TO RELATED APPLICATIONS

This application is a divisional of U.S. Ser. No. 08/098,016, filed Jul. 27, 1993, now U.S. Pat. No. 5,681,713, which is a continuation of U.S. Ser. No. 07/681,222, filed Apr. 5, 1991, now abandoned, which is a continuation-in-part of U.S Ser. No. 07/278,386, filed Dec. 1, 1988, now abandoned, and a continuation-in-part of U.S. Ser. No. 07/574,563 filed Aug. 27, 1990, now abandoned, which is a continuation of U.S. Ser. No. 07/428,454 filed on Oct. 30, 1989, now abandoned which is a continuation of U.S. Ser. No. 07/047,736 filed on May 8, 1987, now abandoned.

FIELD OF INVENTION

The present invention relates generally to expression of heterologous proteins in Drosophila cells and purification of the expressed gene products. In addition, this invention relates to the production of tPA and novel mutant HIV gp160 and gp120 gene products by this expression system.

BACKGROUND OF THE INVENTION

Human immunodeficiency virus type 1 (HIV-1) is the etiological agent of acquired immune deficiency syndrome, also known as AIDS. This retrovirus has a complex genetic organization, including the long terminal repeats (LTRs), the gag, pol, and env genes, and other genes. This retrovirus carries a number of viral antigens which are potential candidates either alone or in concert as vaccinal agents capable of inducing a protective immune response.

Among the more promising of the HIV-1 antigens is the viral envelope glycoprotein (gp160) or specific fragments thereof. The env gene encodes the 160 kilodalton (kd) precursor glycoprotein of the viral envelope. gp160 is cleaved posttranslationally into a 120 kd glycoprotein (gp120) and a 41 kd glycoprotein (gp41), which are present at the virus surface.

These viral glycoproteins assume a tertiary structure as viral spikes protruding outwards from the surface of the viral particle. About 70 to 80 spikes are believed to be associated with each newly synthesized viral particle. As the viral particle ages, the spikes disappear, apparently because the association between the gp120 and gp41 is weak. Thus, for newly synthesized viral particles, this viral glycoprotein spike is believed to be the most immediate target accessible to the immune system following infection.

Virus neutralizing antibodies have been reported directed against gp120 and gp41 epitopes. It has been specifically noted that a target site for type specific neutralizing antibodies is located in the 3' half of the gp120 glycoprotein molecule.

The env gene of HIV-1 has thus been the target of numerous recent investigations. Expression of glycosylated gp160 has previously been obtained in mammalian cells and certain baculovirus insect cells by groups which have also reported the induction of both humoral and cellular immune responses to these antigens. gp120 has been expressed recombinantly with the use of heterologous promoters in several systems. See, e.g., S. Chakrabarti et al, *Nature* (London), 320: 535 (1986); S. I. Hu et al, *Nature* (London), 320: 537 (1986); and M. P. Kieny et al, *Biotechnology*, 4: 790 (1986).

L. A. Lasky et al, *Science*, 233: 209–212 (1986) constructed a number of plasmids containing mutant env genes for tranfection into mammalian cells, specifically Chinese hamster ovary (CHO) cells. These researchers secreted a gene product encoded in a plasmid containing the first 50 amino acids of the glycoprotein D (gD) protein joined in phase to an amino acid sequence (#61–#531) of the env protein, an HBsAg polyA signal, a DHFR gene and the SV40 origin of replication. A recombinant envelope antigen was produced containing 25 amino acids of gD at its amino terminus and lacking 30 residues from the mature processed from of gp120, and also having a deletion of the gp41 sequence (about 20 amino acids of the carboxyl terminus to the actual 160 kd precursor processing site). The resulting gene was 520 amino acids in length. When transfected into CHO cells, the cell-conditioned supernatants contained a 130 kd protein, called gp130.

Fox, *Biotechnology*, 6: 116 (1988) reports the VAXSYN HIV-1 vaccine developed by MicroGeneSys. This report does not disclose any details of this vaccine.

D. L. Lynn, et al, in "Mechanisms of Control of Gene Expression", Eds. Allan R. Liss Inc., pp. 359–368 (1988) disclose the cloning of the entire gp160 gene behind the polyhedron promoter of the baculovirus Autographacalifornica. These insect cells infected with the recombinant virus express a protein that is released from the cell upon lysis. This protein co-migrates with gp160, is not cleaved into gp120 and gp41, and is glycosylated and associated with the cell membrane. When deglycosylated with N-glycanase, the protein had a molecular weight of approximately 96 kd. The recombinant protein was immunoreactive with protein from HIV-infected H9 cells, with antisera to a recombinant fraction of gp120, with gp120 itself, with a peptide fragment of gp41, and with human AIDS sera.

tPA can also be prepared by recombinant DNA techniques. Isolation of mRNA for tPA is disclosed, e.g., by Opdenakker et al., *Eur. J. Biochem.* 12:269 (1982). Isolation of cDNA for part of tPA is disclosed by Edlund et al., *Proc. Natl. Acad. Sci. USA* 80:349 (1983). Cloning of cDNA for tPA in *E. coli* is reported by Pennica et al., *Nature* 301:214 (1983). Cloning of cDNA for tPA in *E. coli* and in Chinese Hamster Ovary cells by application of routine recombinant DNA procedures is disclosed by Goeddel et al., EP-A-93, 619 and by Levinson et al., EP-A-117,059. Goldberg et al., PCT patent application WO85-03949, disclose expression of tPA in *E. coli*. Meyhack et al., EP-A-143,081, disclose expression of tPA in yeast. Robinson, WO84-01786, discloses a modified tPA lacking all or a portion of the carbohydrate moieties present in native tPA.

The development of Drosophila cell cultures which are stable and can be grown under laboratory conditions have been reported. See Schneider, *J. Embryol. Exp. Morphol.* 27:353 (1972). Various vectors systems containing specific coding sequences have been inserted into Drosophila under the control of the Drosophila heat shock promoter or COPIA promoters. DiNocera et al., *Proc. Natl. Acad. Sci. USA* 80:7095 (1983). More recently, mRNA encoding the heat-shock promoters has been translated in Drosophila cells at high rates, McGarry et al., *Cell* 42:903 (1985).

B. J. Bond et al, *Mol. Cell. Biol.*, 6(6): 2080 (1986) disclose the structure of the Drosophila melanogaster actin 5C gene. The report discusses the two transcription start sites of the actin 5C gene and fusions between the promoter sequences and bacterial chloramphenicol acetyltransferase gene inserted into D. melanogaster host cells.

H. Johansen et al, 28th Annual Drosophila Conference, p. 41 (1987) is an abstract by the inventors of the present application which briefly states that *E. coli* gal K genes regulated by a Drosophila metallothionein promoter were expressed in Drosophila cell lines.

A. Vanderstraten et al, Proceedings of the 7th International Conference on Invertebrate and Fish Tissue Culture, Abstract, University of Tokyo Press, Japan, (1987) and A. Vanderstraten et al, in "Invertebrate and Fish Tissue Culture", Eds. Y. Kuroda et al, Japan Scientific Societies Press, Tokyo, pp. 131–134, (1988) are also publications by the present inventors which discuss a hygromycin B selection system.

It is thus an object of this invention to introduce, select and overexpress heterologous genes in a Drosophila expression system.

SUMMARY OF INVENTION

In one aspect, the present invention is a method for expressing a non-bacterial heterologous gene product in Drosophila which comprises transfecting Drosophila cells with a gene expression unit having a promoter of Drosophila origin, and a selection marker; culturing transfected cells under conditions such that the gene product is expressed; and collecting the gene product. The gene expression unit and the selection marker may be located on a single vector or may be located on different vectors.

In related aspects, this invention comprises a non-bacterial heterologous gene expression unit comprising a DNA coding sequence for said protein and a regulatory element having a promoter of Drosophila origin. The gene expression unit may be, but is not limited to, an HIV gene expression unit. In related aspects, the gene expression unit may be, but is not limited to, a tPA, or active variants thereof.

In another aspect, this invention is a DNA vector which comprises the gene expression unit of the present invention.

In yet another related aspect, this invention is a Drosophila cell transfected with the DNA vector of this invention.

In further related aspects, this invention is a vaccine for stimulating protection against HIV infection, which comprises an immunoprotective and non-toxic quantity of the HIV env protein produced by this invention.

Also provided by this invention is a diagnostic agent useful in detecting presence of HIV infection in a sample of biological fluid which contains a Drosophila cell-produced HIV protein of the invention. Additionally, the env protein of the invention may be employed to identify or isolate HIV binding proteins, such as CD4 or derivatives thereof.

Another embodiment of the invention is a method for expressing a heterologous gene product in Drosophila which comprises transfecting Drosophila cells with a gene expression unit having a promoter of Drosophila origin, and a selection marker, wherein the selection marker is hygromycin B phosphotransferase; culturing transfected cells under conditions that the gene product is expressed; and collecting the gene product.

In another embodiment, this invention is a method for expressing a heterologous gene product in Drosophila which comprises cotransfecting Drosophila cells with a gene expression unit for the heterologous gene product and a selection marker, wherein the selection marker is DHFR; culturing transfected cells whereby the copy number of the DHFR gene and the heterologous gene expression unit are expressed without further amplification; and collecting the gene product.

DETAILED DESCRIPTION OF THE INVENTION

The method and expression system of the present invention facilitate high-level production of heterologous proteins, particularly tPA, HIV env proteins, gp120 and gp160, and derivatives thereof in recombinant Drosophila cells. The Drosophila cells are transfected by standard cloning techniques which permit introduction of foreign or heterologous DNA into a host cell without adversely affecting the foreign DNA or the host cell. The recombinant Drosophila cells so constructed produce heterologous proteins, also referred to as heterologous gene products.

In contrast to the Baculovirus system of the prior art, in which the protein of interest is provided only upon lysis of the infected insect cells, the method of this invention provides a continuous cell expression system for heterologous proteins. Upon secretion, said protein is available by purification from the culture medium using conventional techniques. Alternatively, the protein may be produced intracellularly or membrane-bound. The protein may be extracted from the cells using conventional techniques. Alternatively, membrane-bound protein (i.e., asssociated with the outer cell membrane) may be employed in a variety of cell-associated assays.

The present invention is not limited to any particular Drosophila cell line. Preferably the Drosophila cell line for use in the present invention is the D. melanogaster $S_2$ line. $S_2$ cells [Schneider, J. Embryol. Exp. Morph. 27: 353 (1972)] are stable cell cultures of polyploid embryonic Drosophila cells. Introduction of the cDNA coding sequence for gp160, or its subunits gp120 or gp41, or derivatives thereof, into Drosophila $S_2$ cells by DNA transfection techniques produces unexpectedly large amounts of HIV env proteins. Similar results have been achieved for expression of tPA. Use of the $S_2$ Drosophila cell has many advantages, including, but not limited to, its ability to grow to a high density at room temperature. Stable integration of the selection system has produced up to 1000 copies of the transfected gene expression unit into the cell genome.

Other Drosophila cell culture systems may also useful in the present invention. Some possibly useful cells are, for example, the KC-O Drosophila Melanogaster cell line which is a serum-free cell line [Schulz et al, Proc. Nat'l Acad. Sci. USA, 8: 9428 (1986)]. Preliminary studies using the KC-O line have suggested that transfection is more difficult than with $S_2$cells. Another cell line which may be useful is a cell line from Drosophila hydei. Protein expression can be obtained using the hydei cell line; however, transfection into this cell line can result in the transfected DNA being expressed with very low efficiency [Sinclair et al, Mol. Cell. Biol., 5: 3208 (1985)]. Other available Drosophila cell lines which may be used in this invention include $S_1$ and $S_3$.

The Drosophila cells selected for use in the present invention can be cultured in a variety of suitable culture media, including, e.g., $M_3$ medium. The $M_3$ medium consists of a formulation of balanced salts and essential amino acids at a pH of 6.6. Preparation of the media is substantially as described by Lindquist, DIS, 58: 163 (1982). Other conventional media for growth of Drosophila cells may also be used.

A recombinant DNA molecule or vector containing a heterologous protein gene expression unit can be used to transfect the selected Drosophila cells, according to the invention. The gene expression unit comprises a coding sequence for the heterologous gene of interest operatively linked to a promoter of Drosophila origin. For example, a gene expression unit containing a DNA coding sequence for a selected HIV protein or for a derivative thereof. Such derivatives may be obtained by manipulation of the gene sequence using traditional genetic engineering techniques, e.g., mutagenesis, restriction endonuclease treatment, ligation of other gene sequences including synthetic sequences and the like. See, e.g., T. Maniatis et al, *Molecular Cloning, A Laboratory Manual.*, Cold Spring Harbor Laboratory, Cold Spring Harbor, N.Y. (1982).

The HIV DNA coding sequence has been recently published. See, Ratner et al, *Nature* 313:277–284 (1985) or Wain-Hobson et al, *Cell* 40:9–17 (1985). The nucleotide sequence is also available from GenBank (clone BH10, Ratner et al, supra).

DNA molecules comprising the coding sequence of this invention can be derived from HTLV-III infected cells using known techniques (see, Hahn et al, *Nature* 312:166–169 (1984)), or, in the alternative, can be synthesized by standard oligonucleotide techniques. Moreover, there are numerous recombinant host cells containing the cloned DNA coding sequences, which are widely available.

Derivatives can then be prepared by standard techniques, including DNA synthesis. Such derivatives may include, e.g., gp120 or gp160 molecules in which one or more amino acids have been substituted, added or deleted without significantly adversely affecting the binding capacity or biological characteristics of the protein. Derivatives of these proteins may also be prepared by standard chemical modification techniques, e.g., acylation, methylation.

Another example is a tPA (tissue plasminogen activator) gene expression unit which comprises a DNA coding sequence for tPA, or for an active variant thereof. Said variants possess the same or substantially the same active site of tPA. For example, they include, but are not limited to, molecules in which one or more amino acids have been added, deleted, rearranged, or substituted. Such variants also encompass molecules in which one or more functional domains have been added, deleted or altered such as by combining the active site of one plasminogen activator, e.g., tPA, with the fibrin binding domain of another plasminogen activator, e.g., one or more kringle regions from urokinase or plasminogen, or with another fibrin binding molecule such as a Fab fragment of an anti-fibrin IgG molecule (see for example, Runge et al., *Proc Natl Acad Sci*, 84: 7659–7662 (1987).

Other variants include tPA molecules in which the primary amino acid sequence has been altered in the growth factor domain so as to increase the serum half-life of the plasminogen activator. Such tPA variants are disclosed for example, by Browne, EP-A-0,240,334 (Published Oct. 7, 1987), Kalyan et al., W088/05822 (Published, Aug. 11, 1988), and Cassani et al., EP-A-0,308,716 (Published, Mar. 29, 1989; urokinase variants).

Further examples of active variants are hybrids comprising the active site of tPA, e.g. the B chain of tPA, with other sequences, e.g., the A-chain of plasmin, see Robinson et al., U.S. Pat. No. 4,752,581. Another preferred variant is disclosed by Browne et al., EP-A-297,882 (Published Jan. 4, 1989). This molecule, referred to as H37, is a plasminogen (amino acids 1–541)-tPA (amino acids 262–527) hybrid. Other variants include fusions of the active site of tPA to other plasminogen activators, e.g. urokinase, prourokinase, streptokinase.

The tPA coding sequence is available from several sources or can be obtained from human cells or cell lines, such as the Bowes melanoma cell line or the HeLa cell line. Standard techniques of genetic engineering are utilized to derive a tPA coding sequence from the genomic DNA of a human cell.

Also included in the gene expression unit are regulatory regions necessary or desirable for transcription of the HIV protein coding sequence and its subsequent translation and expression in the host cell. The regulatory region typically contains a promoter region which functions in the binding of RNA polymerase and in the initiation of RNA transcription. The promoter region is typically found upstream from the HIV protein coding sequence.

Preferred promoters are of Drosophila origin, e.g., the Drosophila metallothionein promoter [Lastowski-Perry et al, *J. Biol. Chem.*, 260: 1527 (1985)]. This inducible promoter directs high-level transcription of the gene in the presence of metals, e.g., $CuSO_4$. Use of the Drosophila metallothionein promoter results in the expression system of the invention retaining full regulation even at very high copy number. This is in direct contrast to the use of the mammalian metallothionein promoter in mammalian cells in which the regulatory effect of the metal is diminished as copy number increases. In the Drosophila expression system, this retained inducibility effect increases expression of the gene product in the Drosophila cell at high copy number.

The Drosophila actin 5C gene promoter [B. J. Bond et al, *Mol. Cell. Biol.*, 6: 2080 (1986)] is also a desirable promoter sequence. The actin 5C promoter is a constitutive promoter and does not require addition of metal. Therefore, it is better-suited for use in a large scale production system, like a perfusion system, than is the Drosophila metallothionein promoter. An additional advantage is that the absence of a high concentration of copper in the media maintains the cells in a healthier state for longer periods of time.

Examples of other known Drosophila promoters include, e.g., the inducible heatshock (Hsp70) and COPIA LTR promoters. The SV40 early promoter gives lower levels of expression than the Drosophila metallothionein promoter. Promoters which are commonly employed in the cell expression vectors including, e.g., avian Rous sarcoma virus LTR and simian virus (SV40 early promoter) demonstrate poor function and expression in the Drosophila system.

A desirable gene expression unit or expression vector for the HIV protein may be constructed by fusing the HIV protein coding sequence to a desirable signal sequence. The signal sequence functions to direct secretion of the protein from the host cell. Such a signal sequence may be derived from the sequence of tissue plasminogen activator (tPA). Other available signal sequences include, e.g., those derived from Herpes Simplex virus gene HSV-I gD [Lasky et al, *Science*, 233:209–212 (1986)].

The HIV DNA coding sequence may also be followed by a polyadenylation (poly A) region, such as an SV40 early poly A region. The poly A region which functions in the polyadenylation of RNA transcripts appears to play a role in stabilizing transcription. A similar poly A region can be derived from a variety of genes in which it is naturally present. This region can also be modified to alter its sequence provided that polyadenylation and transcript stabilization functions are not significantly adversely affected.

The recombinant DNA molecule may also carry a genetic selection marker, as well as the HIV protein gene functions. The selection marker can be any gene or genes which cause a readily detectable phenotypic change in a transfected host cell. Such phenotypic change can be, for example, drug resistance, such as the gene for hygromycin B resistance (i.e., hygromycin B phosphotransferase).

Alternatively, a selection system using the drug methotrexate, and prokaryotic dihydrofolate reductase (DHFR) gene, can be used with Drosophila cells. The endogenous eukaryotic DHFR of the cells is inhibited by methotrexate. Therefore, by transfecting the cells with a plasmid containing the prokaryotic DHFR which is insensitive to methotrexate and selecting with methotrexate, only cells transfected with and expressing the prokaryotic DHFR will survive. Unlike methotrexate, selection of transformed mammalian and bacterial cells, in the Drosophila system, methotrexate can be used to initially high-copy number transfectants. Only cells which have incorporated the protective prokaryotic DHFR gene will survive. Concomitantly, these cells have the gene expression unit of interest.

An illustrative plasmid produced, according to the present invention, is pgp160Δ32, which contains a gp160 derivative replacing the N-terminal 32 amino acid sequence of gp160 with the first amino acid of tPA, serine. This plasmid is further described in Example 1.

Another such plasmid vector is pgp120FΔ32 which contains gp160 sequence having the first 32 amino acids replaced with serine and containing a carboxyl deletion of 216 amino acids. This plasmid is also described in Example 1.

Still another plasmid which illustrates the derivative proteins of the present invention is pgp120Δ32, which contains the entire coding sequence for gp120 minus the first 32 amino acids at the N-terminal which are replaced with serine. Additionally, plasmid pgp120Δ274 contains a gp120 protein sequence which has replaced the first 274 amino terminal amino acids with the first amino acid of tPA, serine, and containing the remaining amino acids of gp120 up to the processing site of gp160. These vector constructions are described more completely in Example 1.

Once a recombinant DNA molecule or expression vector containing the HIV protein gene expression unit has been constructed, it can be transfected into the selected Drosophila cell using standard transfection techniques. Such techniques are known to those of skill in the art and include, for example, calcium phosphate co-precipitation, cell fusion, electroporation, microinjection and viral transfection.

A two-vector system can be used in the present invention to co-transfect into the Drosophila cell a gene expression unit for the desired heterologous protein and the coding region for the selection system to be used. For example, a preferred illustrative embodiment of this invention is the production of an HIV protein employing a vector containing an HIV protein expression unit, e.g., pgp120Δ32, and a vector containing a hygromycin B gene expression unit, e.g., pCOHYGRO. pgp120Δ32 contains an expression unit comprising the Drosophila metallothionein promoter, a derivative of the gp120 gene, and the SV40 poly A site. This gp120 expression unit in combination with the pCOHYGRO vector system will produce a gp120 derivative in $S_2$ Drosophila cells by maximizing the advantage of hygromycin B resistance for selection. With this system, the antibiotic hygromycin B can be used to select for those cells containing the transfected vectors. A more complete description of this embodiment is described in Example 2.

As another example, an expression system employing the DHFR gene/methotrexate selection system, consisting of the vectors pgp120Δ32 and pHGCO, can be used to select methotrexate-resistant cells expression gp120 or a derivative thereof. The vector pgp120Δ32 comprises a gp120 gene expression unit in which the promoter is the Drosophila metallothionein promoter. The pHGCO vector comprises a DHFR gene expression unit and is co-transfected with the pgp120Δ32 vector, thereby providing the DHFR gene necessary for selection. These selectable markers along with cotransfection of Drosophila cells is further described by Johansen et al, U.S. patent application Ser. No. 07/047,736, filed May 8, 1987 and is incorporated by reference herein.

As another illustrative example, the pDM100 expression system, consisting of the vectors pDM100 and pHGCO, can be used to prepare recombinant $S_2$ cells containing the DNA coding sequence for tPA. The vector, pDM100, comprises a tPA gene expression unit in which the promoter is the Hsp70 heatshock promoter from Drosophila (Ingolia, et al., Cell, 21:669 (1980)). The pHGCO vector comprises a DHFR gene expression unit and is cotransfected with the pDM100 vector thereby providing the DHFR gene necessary for selection. A more complete description of this embodiment of the invention is found in Example 1.

A second illustrative embodiment of this invention is the production of tPA using a two vector method but with a tPA gene expression unit which employs the pCOHYGRO vector system consisting of the vectors pCOHYGRO and pDMtPA.

pCOHYGRO comprises a hygromycin B gene expression unit. pDMtPA contains the tPA gene expression unit using the metallothionein promoter. A tPA gene expression unit which utilizes the pCOHYGRO vector system will produce tPA in $S_2$ Drosophila cells by maximizing the advantage of hygromycin B resistance for selection. With this system, the antibiotic hygromycin B can be used to select for those cells containing the transfected vectors.

According to the invention, the two vectors are co-transfected into the $S_2$ Drosophila cell using the method as described by Wigler et al, Cell, 16: 777 (1979). However, one feature of the present invention is the ability to alter the heterologous gene copy number by varying the ratio of the vectors used in co-transfection. The transfected cells are then selected, such as in $M_3$ medium containing serum and the appropriate selection agent, e.g., hygromycin B or methotrexate.

Another feature of the present invention is that the DHFR gene in Drosophila is used for selection only. That is, the DHFR gene and the gene of interest, integrate into the host cell's genome at a high copy number initially. Therefore there is no need to further amplify the recombinant host cell to increase the gene of interest's copy number. Moreover, the selection of clones expressing a gene of interest is on the order of weeks, compared with months for mammalian hosts.

Once an appropriate vector has been constructed and transfected into the selected Drosophila cell line, the expression of a heterologous protein is induced by the addition of an appropriate inducing agent for the inducible promoter. For example, cadmium or copper are inducing agents for the metallothionein promoter. Heat is the inducing agent for the Hsp70 promoter. For constitutive promoters, such as the actin 5C promoter, no inducing agent is required for expression.

Transcription and expression of the heterologous protein coding sequences in the above-described systems can be monitored. For example, Southern blot analysis can be used to determine copy number of the gp120 gene. Northern blot analysis provides information regarding the size of the transcribed gene sequence [see, e.g., Maniatis et al, cited above]. The level of transcription can also be quantitated. Expression of the selected HIV protein in the recombinant cells can be further verified through Western blot analysis and activity tests on the resulting glycoprotein [see Example 5].

Drosophila $S_2$ cells are especially suited to high-yield production of protein in the method of the present invention. The cells can be maintained in suspension cultures at room temperature (24±10° C.). Culture medium is $M_3$ supplemented with between 5 and 10% (v/v) heat-inactivated fetal bovine serum (FBS). In the preferred embodiment of the invention, the culture medium contains 5% FBS. After induction, the cells are cultured in serum-free media. When the pCOHYGRO vector system is used, the media is also supplemented with 300 µg/µl hygromycin B. In this media, the $S_2$ cells can be grown in suspension cultures, for example, in 250 ml to 2000 ml spinner flasks, with stirring at 50–60 rpm. Cell densities are typically maintained between $10^6$ and $10^7$ cells per ml. In one embodiment of this invention, the cells are grown prior to induction in 1500 ml spinner flasks in media containing 5% serum.

Following cell culture, the heterologous proteins can be isolated from the spent media by known techniques, e.g., by use of a monoclonal antibody affinity column. Other known protein purification steps, e.g., metal chelates, various affinity chromatography steps or absorption chromatography, can be used to purify the heterologous proteins from the culture media. The use of the cell line $S_2$ which secretes the gene product directly into the media is an important feature of the present invention. Direct secretion into the media allows utilization of an efficient one-step purification system. For example, using a monoclonal antibody column directed against the HIV protein, the spent culture media can be added directly to the column and the protein eluted using 1.5 M KSCN in phosphate-buffered saline (PBS).

A preferred purification technique enabling large-scale efficient production of the HIV proteins of the invention employs an immunoaffinity column containing a monoclonal antibody directed against an epitope present in gp160 and present in mature secreted gp120 proteins. Such a monoclonal is advantageous because of its capacity to recognize the protein sequence in more than one configuration. An antibody having these characteristics and useful in immunoaffinity columns for various HIV proteins, derivatives or fragments thereof is designated 178.1. This monoclonal antibody is described in greater detail in Example 3. Such a column of the invention may be made by coupling an antibody with the characteristics of 178.1 to a conventional absorbent carrier, such as Sephadex, under appropriate conventional conditions of pH, temperature and the like. Such a purification column and procedure may be utilized to separate the HIV proteins and fragments of the present invention.

Other monoclonal antibodies may be used in this purification procedure. A variety of monoclonal antibodies which are capable of binding to HIV proteins, particularly gp160 or gp120, have been described in the art and are available. Other new monoclonal antibodies useful in this invention may be developed by now-conventional techniques.

The proteins produced by Drosophila cells, according to this invention, are completely free of contaminating materials, e.g., mammalian, yeast, bacterial and more importantly, other viral materials. Drosophila-produced HIV proteins, and tPA, have also been demonstrated to possess different pattern of glycosylation than that reported by other systems, e.g., mammalian systems.

In addition, the Drosophila cell system has been used to produce entirely single chain tPA. The ratio of long to short form at the amino-terminus is found to be completely opposite to that found in mammalian system. Preliminary gel mobility studies indicate the Drosophila tPA also differs in glycosylation. Because the human tPA is being produced in an insect system, the tPA is completely free of human, hamster or mouse contaminating materials. In addition, human tPA made in Drosophila is free of mammalian retroviruses.

The HIV proteins and derivatives produced, according to the present invention, may be useful in a variety of products. For example, these recombinant proteins may be used in pharmaceutical compositions for the treatment of HIV-infected subjects. Such a pharmaceutical composition, according to the present invention, comprises a therapeutically effective amount of the HIV protein or derivative of the invention in admixture with a pharmaceutically acceptable carrier. The composition can be systemically administered either parenterally, intravenously or subcutaneously. When systemically administered, the therapeutic composition for use in this invention is in the form of a pyrogen-free, parenterally acceptable aqueous solution. The preparation of such a parenterally acceptable protein solution, having due regard to pH, isotonicity, stability and the like, is within the skill of the art.

The dosage regimen will be determined by the attending physician, considering various factors which modify the action of drugs, e.g., the condition, body weight, sex and diet of the patient, the severity of any infection, time of administration and other clinical factors. The pharmaceutical carrier and other components of a pharmaceutical formulation would be selected by one of skill in the art.

Additionally, the recombinant proteins of the present invention may be used as components of vaccines to innoculate mammalian subjects against HIV infection. Immunoprotective refers to an amount sufficient to protect an individual against exposure to the HIV-1 virus. These proteins may be used alone or with other recombinant proteins or therapeutic vaccinal agents. Components of such a vaccine would be determined by one of skill in the art.

Finally, the proteins of the present invention may be useful as diagnostic agents for the detection of the presence of HIV infection or antibodies to an HIV infective agent in biological fluids, such as blood, serum, saliva and the like. These proteins of the invention may also be employed in methods to identify and/or isolate HIV-binding proteins or other HIV-binding substances in biological fluids and tissues, e.g., sCD4 or derivatives thereof. The proteins may thus be components in kits to perform such methods. To identify an HIV-binding substance, a protein, according to the invention, is employed to contact the substance or an impure mixture containing the substance under conditions to promote binding between the protein and the HIV-binding substance. A conventional assay to detect the occurrence of binding, e.g., detection of radioactive labels or the like, is also part of the method. The presence of binding between the protein and the binding substance is, therefore, indicative of HIV binding.

Similarly, in a method to isolate an HIV-binding substance from the mixture, the binding event could be followed by a conventional procedure to purify the bound entity formed by the protein of the present invention and the HIV-binding substance from the mixture. Other components of such diagnostic systems and kits may be conventional components of diagnostic kits and may be selected by those of skill in the art.

Although the preceding description and the examples which follow are directed primarily to expression HIV proteins and tPA in Drosophila, the expression vectors and the two vector expression systems described herein can be used to clone and express other genes and coding sequences in Drosophila. For example, a coding sequence for growth hormones, lymphokines, urokinase, antigenic proteins (e.g. *P. falciparum* CSP, *B. burgdorferi* OspA and OspB, Varicella Zoester Virus glycoproteins, gpI, gpII, gpIII, etc.) or other gene products of interest can be inserted within a gene expression unit into a vector such as pDM100 or pDMtPA and cotransfected with a vector such as pHGCO or pCO-HYGRO. Transfected cells can then be selected as described above.

The following examples illustrate the construction of exemplary vectors and transformants of the invention, and assays for determination of the production level of tPA and the HIV-glycoproteins gp120 and gp160. These examples are not to be considered as limiting the scope of this invention.

Restriction enzymes and other reagents were used substantially in accordance with the vendors' instructions.

EXAMPLES

Example 1

Vector Constructions a) pDMKΔH

As the basic vector for gene expression in Drosophila pML2 was used, which is a small pBR322 vector containing the β-galactamase gene (Mellon et al., Cell 27:297 (1982)). This vector was digested with Sal I which creates a unique cut in the plasmid. Into this site was inserted a Sal I casette containing the SV40 early promoter followed by the galactokinase gene and the SV40 early polyadenylation site.

The Sal I casette was obtained from pDSPI (Pfarr et al., DNA 4:461 (1985)). The orientation of the insert was determined by fine restriction analysis using HindIII and BamHI. The new construct pDMK has the transcription unit for the galactokinase and β-lactamase gene running in the opposite direction. pDMKΔH was created by a deletion of a HindIII site in the pBR322 sequence 5' to the SV40 early promoter. pDMK was digested with HindIII and the site was endfilled (Maniatis, supra) and the vector was religated. pDMKΔH now has a unique HindIII site positioned between the SV40 early promoter and the galactokinase gene.

b) pDMKHSP pDMKΔH was digested with SmaI and HindIII which drops out the SV40 early promoter. The HindIII site was end-filled and the Drosophila HSP70 promoter fragment was inserted into this vector.

The fragment used was a 460 bp fragment obtained by XbaI and XmnI digestion of pDM301 (McGarry, et al., Cell 42:903 (1985)). This fragment contains what is thought to be the regulatory sequences for heat induction. The fragment was endfilled and ligated to the SmaI, HindIII cut vector.

The ligated DNA was transformed into E. coli and colonies containing the desired plasmid were identified by fine restriction of minipreparations of DNA with HindIII and XhoI.

c) pDM100 pDMKHSP was cut with XbaI, then endfilled and finally cut with HindIII. This drops out the galactokinase gene. The tPA coding sequence was isolated from a cDNA clone obtained from Schleuning, et al., supra, on a HindIII-BalI fragment which includes the prepropeptide and the entire coding sequence of tPA. This fragment was inserted into the cut pDMKHSP vector. The ligated DNA was transformed into E. coli and the correct plasmid was identified by restriction with the enzymes HindIII, BamHI and XbaI. Conditions for all restrictions were as recommended by manufacturer (New England Biolabs).

d) pUCOPIA

The 5'LTR from an integrated COPIA element (357 base pairs) was cloned into the BAMHI site of vector pUC18 resulting in the vector designated pUCOPIA. COPIA is a representative member of the disperse middle repetition sequences found scattered through the Drosophila genome (Rubin, et al. in Cold Spring Harbor Symp. Quant. Biol. 45:619 (1980)).

e) pMTtPA

As the basic vector for gene expression in Drosophila, the tPA expression vector pMTtPA (also called pDMtPA) was used. This vector is a derivative of vector pML1, a small pBR322 vector containing the beta-lactamase gene which has deleted the poison sequences [Mellon et al, Cell, 27: 297 (1982)]. These sequences are inhibitory to amplification of the vector. This vector was digested with Sal1 and Aat2 which removes a small piece of pBR322, and the digested ends were filled in. The missing piece of pBR322 is then replaced with a cassette containing the Drosophila metallothionein promoter [see e.g., Lastowski-Perry et al. J Biol Chem, 260:1527 (1985)], on an end-filled EcoR1-Stul fragment, followed by a filled-in HindIII-Sac1 fragment from pDSPI [D. S. Pfarr et al, DNA, 4(6): 461 (1985)] containing a tPA sequence containing the signal sequence, prepeptide and the entire coding region of tPA. The tPA gene on this fragment is followed by an SV40 early polyadenylation site.

f) pgp160Δ32

A HindIII-Xba1 fragment containing the entire env gene was isolated from an HIV-isolate clone BH10 [L. Ratner et al, cited above]. The entire gp160 sequence was then inserted into a Nco1-Xba1 digested vector pDSP1. The resulting vector, SU2, was digested with Nde1, followed by treatment with mung bean nuclease and subsequently digested with Sac1, thus isolating the gp160 gene. The digestion with Nde1 cut the gp160 sequence at amino acid #32. The Sac1 digestion cuts 3' of the gp160 gene, including in the sequence part of the original pDSP1 vector containing a polylinker. This fragment was inserted into the above-described expression vector pMTtPA which had been digested with BglII, end-filled, and subsequently cut with Sac1, which deletes the mature tPA sequence. The BglII site is positioned at the first amino acid of tPA. Consequently, the resulting vector pgp160Δ32 codes for a modified gp160 protein which has replaced the N-terminal 32 amino acids of gp160 with serine.

g) pgp120FΔ32

Another vector containing a modified gene sequence coding or HIV-1 surface glycoprotein gp160 was constructed by digesting pgp160Δ32 with HindIII and Sac1, thereby removing the carboxyl terminal of gp160. Approximately two-thirds of the sequence coding for gp41 is removed by this digestion. Thus, this gp160 sequence is missing the first 32 amino acids and the last 216 amino acids of the natural gp160 sequence. The deleted sequence was replaced by a short synthetic linker sequence coding for a stop codon on an HindIII-Sac1 fragment. The 6-amino-acid linker sequence is as follows: 5'AGCTTTGACTGACTGAGCT 3'.

h) pgp120Δ32

Yet another vector containing a mutant gp160 gene was constructed by digesting pgp160Δ32 with Sty1 and Xba1, thereby deleting all of the sequence of protein gp41 and about 30 amino acids at the carboxyl terminus of the gp120 glycoprotein sequence. This fragment was replaced by a synthetic Sty1-Xba1 linker sequence coding for the correct carboxyl terminus from the Sty1 site to the processing site of gp120-gp41. This sequence was followed by a stop codon. This sequence thereby contained all of the coding sequence for gp120 minus the first 32 amino acids and none of the gp41 coding sequence.

i) pqp120Δ274

Still another exemplary vector containing a mutant gp120 gene was constructed as follows: a 720-base pair carboxyl terminal fragment of gp120 was isolated by partial digestion of pgp120Δ32 with BglII followed by XbaI digestion. This fragment was now inserted in place of the tPA gene into the BglII-Xba1 cut pMTtPA expression vector. The resulting vector p120Δ274 codes for a gp102 protein which has replaced the first 274 amino terminal amino acids with the first amino acid of tPA, serine.

j) pCOHYGRO

A commercially available plasmid, pUC18 [BRL] containing a BaHI and SmaI site was used. The 5' LTR from an integrated COPIA element (357 base pairs) was cloned into the BamHI site of vector pUC18, resulting in the vector designated pUCOPIA. COPIA is a representative member of the disperse middle repetition sequences found scattered through the Drosophila genome [Rubin et al, in *Cold Spring Harbor Symp. Quant. Biol.*, 45: 619 (1980)]. The vector pUCOPIA was cut at the SmaI site and the *E. coli* gene coding for hygromycin B phosphotransferase (hygromycin B cassette) was cloned into pUCOPIA using standard cloning techniques. The hygromycin B cassette was isolated on a HindIII-BamHI fragment of 1481 base pairs from the vector DSP-hygro [Gritz et al, *Gene*, 25: 179 (1983)]. The hygromycin B cassette contains the sequence coding for the hygromycin B phosphotransferase gene and the SV40 early poly A region. The HindIII and BamHI sites were filled in using $T_4$ DNA polymerase, and the hygromycin B cassette was ligated into the SmaI site of the vector pUCOPIA producing vector pCOHYGRO.

Example 2

Transfection into Drosophila $S_2$ Cells 1) tPA: pDM100 was cotransfected into $S_2$ Drosophila cells together with pHGCO which is a plasmid containing the *E. coli* derived procaryotic DHFR gene driven by COPIA 5'LTR (Bourouis et al., *EMBO* 2:1104 (1983)). The transfection procedure was substantially as described by Wigler et al., *Cell* 16:777 (1979). 20 μg plasmid DNA pDM100+ pHGCO was cotransfected in varying ratios depending upon the copy number desired onto $3 \times 10^6$ cells and the precipitate was left on the cells for 18 hours. The cells were then washed and allowed to grow 48 hours to allow expression of DHFR. Cells were spun down and resuspended in medium containing $2 \times 10^{-7}$M methotrexate to select for transformants expressing the DHFR gene. Stable transformants were obtained after 6 weeks selection.

Analysis of Gene Product

Resistant cells were seeded at a density of $5 \times 10^6$ cells/ml in $M_3$ medium without serum. The cells were allowed to express tPA for 3 days before the media was collected and assayed for the presence of tPA protein. Western analysis substantially as described by Bittner, et al., *Ann. Biochem.* 102:549 (1980) showed the presence of high amounts of tPA protein, i.e. the protein has the expected molecular weight (approx. 70 kd) for single chain tPA. Confirmation that the tPA protein was expressed and active was confirmed using the S2251 activity assay. Ranby, et al., *Thromb. Res.* 27:743 (1982).

Southern analysis of the tPA producing polyclonal cells showed that they contained up to 1000 copies of the tPA gene expression unit per cell and that the tPA gene expression unit is amplified and integrated in the host chromosomes in a head to tail pattern.

pCOHYGRO was cotransfected into $S_2$ Drosophila cells together with pDMtPA carrying the tPA gene under the control of the Drosophila metallothionein promoter. The transfected cells were selected in $M_3$ medium with serum containing 300 μg/ml of hygromycin B. After 2 to 3 days under identical conditions the untransfected cells stop dividing and begin to die. The time of selection in order to obtain stable, growing hygromycin B resistant cells in the transfected cultures was approximately two to three weeks.

To obtain cultures having integrated into their chromosomes different copy numbers of the tPA gene, the rations of the two vectors were varied at transfection as indicated in Table 1.

TABLE 1

| pDMtPA | pCOHYGRO | Isolated polyclonal Culture | Approx. Copy Number Hygromycin B Gene | tPA Gene |
|---|---|---|---|---|
| 10 μg | 10 μg | A | 50–100 | 30–40 |
| 18 μg | 2 μg | B | 50–100 | 150 |
| 20 μg | 0.2 μg | C | 50–100 | 2000 |

Expression of tPA was verified after induction of the metallothionein promoter with 10 μM cadmium. A specific tPA mRNA of approximately 2.4 kb was detected by Northern blot analysis. Concomitantly, Western blot analysis of the spent supernatant rom the induced cell cultures revealed a single tPA band at approximately 70 kd.

The level of tPA in the cell supernatants was measured using the S2251 Activity Test. $5 \times 10^6$ cells were seeded in 1 ml of $M_3$ medium without serum and induced for 3 to 4 days. The level of tPA measured in the supernatant is indicated in Table 2.

TABLE 2

| polyclonal culture | uninduced cells (ng/ml) | induced cells (ng/ml) |
|---|---|---|
| A | 160 | 500 |
| B | 99 | 1500 |
| C | 85 | 1300 |
| control pCOHYGRO | 0 | 0 |

Scale up of polyclonal culture B along with two single clone cultures derived from polyclonal culture B using standard soft-agar cloning techniques resulted in significant increase in tPA production as shown in Table 3.

TABLE 3

| Cell Culture | Copy Number | μg/ml (afer 3 days) |
|---|---|---|
| polyclone culture B | 100–500 | 14–20 |
| single clone T | 30 | 3–12 |
| single clone I | 150 | 22–37 |

Cells were maintained as suspension cultures in 250 ml to 2000 ml spinner flasks Culture medium was M3 supplemented with 300 μg/ml hygromycin B. Cultures were incubated at 24±1° C. and stirred at 50–60 rpm. Cell densities were typically maintained between $10^6$ and $10^7$ cells per ml.

For induction, cells were harvested by low-speed centrifugation and resuspended at a density of $5 \times 10^6$ cells per ml in $M_3$ medium supplemented with hygromycin B. Cadmium chloride was added to a final concentration of 10 μM, and the cultures were allowed to grow for 3 to 4 days in serum free media prior to harvesting the tPA.

2) HIV proteins: pCOHYGRO was co-transfected into $S_2$ Drosophila cells together with one of the vectors carrying a gp160 mutant gene under the control of the Drosophila metallothionein promoter as described above. For purposes of this example, the vector employed is pgp120Δ32. The transfected cells were selected in $M_3$ medium containing 5% serum and 300 μg/ml of hygromycin B. After 2 to 3 days under identical conditions, the untransfected cells stop dividing and begin to die. The time of selection in order to obtain stable, growing hygromycin B-resistant cells in the transfected cultures is approximately two to three weeks.

To obtain cultures having integrated into their chromosomes different copy numbers of the gp120 mutant gene, the ratios of the two vectors were varied. The ratio in this example was 20:1. Similar ratios have been employed for other gp160 mutant vectors of this invention. This ratio is the same when any of the gp160 mutant vectors are used.

Expression of the pgp120Δ32 gene product was verified after induction of the metallothionein promoter with 500 μM $CuSO_4$. Western blot analysis of the spent supernatant from the induced cell cultures revealed a single band at approximately 100 kd.

The level of the mutant gp160 gene product in the cell supernatants was measured using the gp120 ELISA assay, described in Example 4, and using purified viral gp120 as standards. $5 \times 10^6$ cells/ml were seeded in $M_3$ medium without serum and induced for 3 to 4 days. The level of gp120 measured in the supernatant is approximately 1–2 mg/l.

Cells were maintained as suspension cultures in 250 ml to 2000 ml spinner flasks. Culture medium was $M_3$ supplemented with 300 mg/ml hygromycin B. Cultures were incubated at 24±1° C. and stirred at 50–60 rpm. Cell densities were typically maintained between $10^6$ and $10^7$ cells per ml in $M_3$ medium supplemented with hygromycin B. $CuSO_4$ was added to a final concentration of 500 μM, and the cultures were allowed to grow for 3 to 4 days in serum-free media prior to harvesting the modified gp120 glycoprotein.

The proteins, according to this method produced, were approximately 100 MW, and the level of expression was higher than any other reported gp120/gp160 expression in any eukaryotic cell system. In standard biological activity assays, the purified modified gp120 expressed, as described above, is capable of inhibiting virus infection in tissue culture, binds $T_4$ and reacts to antibodies to gp120.

It is expected that one of skill in the art could express the other gp160 and gp120 proteins and fragments thereof, described by the present invention, using substantially the same systems and procedures as exemplified above for the protein fragment encoded in pgp120Δ32.

Example 3
Monoclonal Antibody 178.1

An affinity purification column employing a novel monoclonal antibody was used in the purification scheme applied to the above-described mutant gp160/gp120 proteins. This monoclonal antibody may be characterized as being capable of reacting with non-denatured HIV glycoprotein products present in cell lysate and with mature gp120 as secreted into the supernatant of a yeast culture. One such monoclonal antibody specific for the epitope which is contained both in the unprocessed gp160 recombinant molecule and in the full-size processed gp120 protein is a mouse monoclonal antibody 178.1.

An expression system employing the *C. albicans* glucoamylase promoter and signal peptide was employed to produce partially purified yeast-recombinant gp160 for production of 178.1. The production of this yeast-derived gp160 is described in co-owned, co-pending Bruck et al, U.S. patent application Ser. No. 07/236,699, filed Aug. 25, 1988. This application is incorporated herein by reference.

Eight-week-old Balb/c mice were injected three times subcutaneously and intraperitonally with the partially purified (1.5–3% purity) yeast-recombinant gp160 in Freund's adjuvant at 4-week intervals. After a resting period of 3 months, one mouse was sacrificed, and its spleen cells were fuse with myeloma cells [see, e.g., R. P. Siraganian et al, *Meth. Enz.*, 92: 17 (1983); EMBO Course on Hybridoma Production, Basel Inst. for Immunol. (1980)]. The myeloma cells used are a subclone of the $Sp_2/O-Ag14$ line previously selected for optimal growth in agar medium and high fusion efficiency [J. D. Franssen et al, *Proc. XXIX Collog. Protids Biol. Fluids*, 29: 645–649 (1981)]. After about ten days, supernatants were withdrawn for screening in a capture ELISA, using a commercial monospecific anti-gp120 reagent [Biochorm, Seromed Ref. D7324] as capture antibody.

Briefly, Nunc Immunoplate I (nr 4-39454) were coated overnight at 4° C. with 50 μl of a solution of 5 μg/ml of sheep anti-gp120 IgGs in PBS. The plates were washed with washing buffer (PBS, Tween 20 0.1%) and saturated with 100 μl of saturation buffer [PBS, Newborn Calf Serum 4%, bovine serum albumen (BSA) 1%, Tween 20 0.1%] for 1 hour at 37° C. Fifty μl/well of crude $Molt_3/HTLV-III_B$ or $Molt_3$ cell lysate ($10^7$ cells/ml in PBS, Triton X-100 1%) or of the supernatant fraction (S2-30) of the recombinant-yeast gp160 (or similarly-treated negative control) were used as antigen and incubated in the plates for 3 to 5 hours at room temperature. The plates were washed extensively, and 50 μl of hybridoma supernatants were added to each well and incubated overnight at 4° C. After a washing step, 50 μl/well of a 1/500 dilution of biotinylated anti-mouse immunoglobulins (Igs) (Amersham Ref. RPN 1021) in saturation buffer were incubated in the plates for 1 hour at 37° C. The plates were washed again, and 50 μl/well of a 1/1000 dilution of streptavidin biotinylated horseradish peroxidase complex (Amersham Ref. RPN 1051) in saturation buffer were added to each well.

After an additional washing step, 50 μl of a solution of 0.4 mg/ml of orthophenylene diamine dihydrochloride (OPD, Sigma P1526) and 1 μl/ml of $H_2O_2$ (30% in citric/Na citrate 0.1 M pH 5) supplemented with 0.1% Tween 20 were added to each well. The plates were then incubated for 20 minutes at room temperature in the dark, and the reaction was stopped by addition of 50 μl/well of 2M $H_2SO_4$. The optical density at lambda=492 nm was monitored, and 50 positive clones were selected for further subcloning in soft agarose, according to P. Herion et al, *Proc. XXIX Collog. Protids Biol. Fluids*, 29: 627 (1981). The cloned hybridomas were then grown in vivo by injecting 2 to $5 \times 10^6$ hybridoma cells in the peritoneal cavity of Balb/c mice pretreated by intraperitoneal injection of pristane (2, 6, 10, 14-tetramethyl pentadecane).

The monoclonal antibodies selected from the above procedure were characterized by Western blot analysis (WB), radioimmuno precipitation assay (RIPA), purification, biotin-labeling and competition assays. Resulting monoclonal antibodies were further characterized by analysis of their reactivity toward various recombinant and native antigens.

A high yield of hybridomas was obtained by this procedure. More than 200 wells were positive in the screening assays. However, among them, only 50 wells were selected and after cloning, the cells were expanded in ascitic acid. All the ascitic fluids were tested in WB and RIPA. Among the 39 monoclonals tested, 37 showed a gp160 band in RIPA. None reacted with the gp120 form in the same assay. Those monoclonal antibodies that displayed only gp160 recognition in RIPA, while being clearly reactive to gp120 in WB, were analyzed by subclass. Three monoclonals that were IgG2A were purified on a protein A-sepharose column and biotin-labeled. Competition assays using vaccinia gp160 as antigen were performed, and the obtained result defined at least five different groups of epitope recognition with the gp160 protein. Monoclonal 178.1 was selected for an epitope present on mature gp120 and unprocessed intracellular gp160.

A Western blot (WB) analysis was performed according to conventional techniques to demonstrate that 178.1 is capable of binding HIV virus isolated from human cells infected with HTLV-III$_B$ [Molt$_3$/HTLV-III$_B$].

Radio immuno precipitation assays (RIPA) were performed, as described in P. J. Kanki et al, *Science*, 228: 1199 (1985) to demonstrate that 178.1 could immunoprecipitate the human cells infected with HTLV-III virus strains.

The reactivity of the monoclonal antibodies recognizing non-overlapping epitopes towards a large panel of antigens was assessed using a sandwich ELISA involving sheep anti-gp120 as capture reagant. Monoclonal antibody 178.1 was negative in ELISA on divergent HIV isolates Molt$_3$/ HTLV-III$_B$, H9/HTLV-III$^{PF1}$ and Hut78/ARV$_2$, while clearly positive when tested on HTLV-III$_B$ in RIPA, WB, or ELISA using recombinant antigens. This monoclonal recognizes an epitope that is apparently conserved between gp160 and gp120 and thus, when used in the purification technique described in Example 4 below, provides an added advantage for the production of gp160/gp120 glycoproteins in various constructs.

Example 4

Purification of gp120Δ32 from Drosophila-conditioned Cell Culture Medium

The recombinant gp120 protein from Example 2 was purified as follows: 30 liters of Drosophila-conditioned media (CM) containing gp120Δ32 was made with 1 mM phenylmethylsulfonyl fluoride (PMSF), 10 mM ethylenediamine tetraacetic acid (EDTA) and 70 Kallikrein inhibitor units. CM was filtered through a 0.45 μm Durapore membrane using a pellicon (Millipore) device. Filtered CM was applied to S-sepharose fast flow (Pharmacia) (5 liters; 25.2 cm×11 cm) at a linear flow rate (LFR) of 37 ml/cm² hr equilibrated in Buffer A, containing 20 mM 2-[N-morpholino]ethanesulfonic acid (MES), pH 6.0. After application of all CM, the column was eluted in one step with Buffer B, containing 20 mM MES, pH 6.0, 0.4M NaCL.

The S-sepharose-eluted gp120Δ32 was applied to an anti-gp120 mouse monoclonal-sepharose 4B column (60 ml; 3.2 cm×6.5 cm) at a LFR of 10 ml/cm²hr. This column was equilibrated in Buffer B. After application of one-half S-sepharose pool, the column was washed with 1 column volume of Buffer B, 2 column volumes of 20 mM MES, pH 6.0, 1.0M NaCL (Buffer C), and 2 column volumes of Buffer A. gp120Δ32 was eluted with 0.1M acetic acid, pH 2.8, and fractions were immediately neutralized by addition of 0.1 volumes of 1M Tris (hydroxymethyl)aminomethane (Tris), pH 10.4.

Mouse anti-gp120 monoclonal antibody hybridoma 178.1 was produced according to Example 3 above. This hybridoma was seeded at 2×10⁵ cells/ml and cultured for four days in Dulbecco's Modified Eagle Medium [Hazelton Research Products] supplemented with 4.5 grams/liter glucose, 2 μM glutamine and 10% serum. CM containing 178.1 antibody was filtered (0.2 μm membrane) and applied to a protein A-sepharose (Pharmacia) (17 ml; 1.5 cm×10 cm) equilibrated in 0.1M Tris, pH 8.2. Antibody was eluted with 0.1M sodium citrate, pH 3.5 and immediately neutralized with Tris.

Purified anti-gp120 monoclonal antibody was coupled to CNBr-activated sepharose 4B (Pharmacia), according to manufacturer's instructions at a density of 2 mg antibody/ml resin and with a coupling efficiency of 98%, resulting in an anti-gp120-sepharose-affinity resin. This affinity resin will specifically bind gp120 protein through the interaction of the antibody with a unique structural epitope on gp120.

The purity of the final gp120 protein product, according to this purification technique, is 80–90% with an estimated yield of 8.5 mg/30 liters conditioned media. Recovery is estimated at between 25–50%.

This purification technique and affinity resin is also believed to be effective with other HIV proteins or fragments thereof having this epitope.

Purification of tPA from Conditioned Cell Culture Media

PAM-2 Sepharose® (American Diagnostica, Greenwich, Conn.) is tPA monoclonal antibody coupled to Sepharose 4B. 5 ML of PAM-2 Sepharose (approximately 10 mg monoclonal tPA antibody per column volume) was transferred to a 1×6 cm column and washed with 2M KSCN at 5 ml/hr. overnight to remove loosely bound monoclonal antibody. After washing, 50 ml of phosphate buffered saline (PBS) was passed through the column to equilibrate the gel.

The sterile filtered conditioned media from the induced Drosophila cells (1 liter) was slowly passed through the column at 0.8 ml/min. The column was then washed with 30 ml of PBS followed by 30 ml 0.5 M KSCN in PBS at 0.8 ml/min. The tPA was eluted using 30 ml of 1.5 M KSCN followed by 2.0 M KSCN at a flow rate of 0.8 ml/min. Greater than 90% of the tPA eluted in a single peak with 1.5 M KSCN. Following the elution with 2.0 M KSCN in order to elute any residual, tightly binding tPA, the column was washed with 30 ml PBS then stored in 0.01% Sodium Azide in PBS.

An analysis of the tPA produced in the Drosophila cells showed a direct correlation between the cell density at time of induction and the amount of tPA produced. It was found that induction of cells at a density 5×10⁶ greatly increased the concentration of tPA being secreted into the media.

Example 5

Assay

The assay described below is a non-isotopic assay utilizing an enzyme and a substrate for the detection of gp120 or fragments thereof, which was employed in detecting the gp120 proteins produced by the methods and compositions of the present invention.

In the assay, the criteria for detecting gp120 is dependent on antibody specificity. An anti-gp120 monoclonal antibody [DuPont, Cat. No. 9284], diluted in 0.1M sodium carbonate buffer (pH 9.5) to two mgs/ml, is used to capture the gp120 protein. 100 ml of this antibody dilution is added to each well in duplicate in an assay plate, except for those wells designated as controls. The plates were incubated at 4° C. overnight. The antibody was washed-out the following day and the plate blocked by adding 300 ml of blocking buffer consisting of 1% BSA in PBS to each well for 1 hour at room temperature.

The viral gp120 standards were diluted to 1 μg/ml, 0.5 μg/ml, 0.25 μg/ml, 0.1 μg/ml, and 0.2 μg/ml in a washing buffer consisting of PBS and 0.05% Tween 20. 100 ml of the diluted standards are added to each well in duplicate. The plates were incubated on a plate shaker for 2 hours at room temperature, and thereafter, each plate was washed four times with washing buffer.

To each well, 100 μl of rabbit anti-gp120 antibody (described by DeBouck et al, U.S. patent application Ser. No. 07/056,553, filed May 29, 1987) diluted 1/1000 in washing buffer was added and each plated incubated on a shaker for 1 hour. This second antibody sandwiches th gp120 between the two antibodies. The plates were, thereafter, washed four times with washing buffer. To detect this complex, a third antibody, 100 μl of peroxidase (POD) labeled goat anti-rabbit antibody (mostly IgG and IgM antibody) diluted in washing buffer with no azide, is added to each well. The plates were then incubated for 2 hours on a shaker at room temperature.

After the plates were washed four times, 100 μl of a colorless substrate (1 mg/ml of OPD in citrate buffer with 4 μl of 35% hydrogen peroxide per 10 ml of buffer) was added. The hydrogen peroxide was added just prior to adding substrate to the wells. These plates were incubated for 8 minutes on a shaker and the reaction stopped by adding 100 μl of 0.1 M sodium fluoride to each well. In the presence of peroxidase-conjugated antibodies, the substrate turns deep yellow. Optical density, or intensity of the color, which is proportional to the amount of gp120 captured, was read on a plate reader at 450 nanometers, and a standard curve was constructed with concentrations of unknowns calculated. The amount of gp120 in the supernatant culture was determined by comparison to this standard curve.

The tPA concentration was determined using various standard assays including HPLC, the S2251 Assay, the particle fluorescence immunoassay (PCFIA) performed according to the protocol provided by the manufacturer (Pandex Laboratories, Inc. Mundelein, Ill.), and the enzyme immuno-assay (EIA) performed substantially as described in the protocol provided by the manufacturer (American Diagnostica).

Using the S2251 assay, the activity of the purified tPA has been found to be at least the same as the highest reported for expression in mammalian cells.

The above description and examples fully disclose the invention, including preferred embodiments thereof. Modifications of the methods described, e.g, employing other truncated gp160/gp120 sequences that are obvious to one of ordinary skill in the art of molecular genetics and related sciences, are intended to fall within the scope of the following claims:

What is claimed is:

1. A gene expression unit comprising a DNA coding sequence for a non-bacterial heterologous protein selected from the group consisting of a protein of mammalian origin and a protein of mammalian virus origin, and a regulatory element for transcription of said DNA sequence and translation within a Drosophila cell wherein said regulatory element comprises a Drosophila metallothionein promoter.

2. A DNA vector comprising the gene expression unit of claim 1.

3. A Drosophila cell transfected with the vector of claim 2.

4. A method for expressing a heterologous gene product in Drosophila which comprises: transfecting Drosophila cells with a selection marker and a gene expression unit having both a promoter of Drosophila origin and a DNA sequence encoding said heterologous gene product, wherein said selection marker is hygromycin B phosphotransferase to produce transfected cells; and culturing said transfected cells under conditions such that the gene product is expressed.

5. The method of claim 4 wherein the selection marker is located on a first vector and the gene expression unit for the heterologous gene product is located on a second vector, such that the Drosophila cells are co-transfected with said first and second vectors.

6. The method of claim 5 wherein said first vector is pCOHYGRO.

7. The method of claim 4 wherein the Drosophila promoter is inducible.

8. The method of claim 7 wherein the Drosophila promoter is the metallothionein promoter.

9. The method of claim 7 wherein the Drosophila promoter is the Hsp-70 promoter.

10. The method of claim 4 wherein the Drosophila promoter is constitutive.

11. The method of claim 10 wherein the Drosophila promoter is the actin 5C promoter.

12. The method of claim 10 wherein the Drosophila promoter is the 5'LTR of a COPIA element.

13. A method for expressing a heterologous gene product in Drosophila cells which comprises: co-transfecting Drosophila cells with a first vector comprising a selection marker, wherein the selection marker is hygromycin B phosphotransferase, and a second vector comprising a gene expression unit having a promoter of Drosophila origin operably linked to a DNA sequence encoding the heterologous gene product to produce transfected cells, and culturing said transfected cells under conditions such that the gene product is expressed.

14. The method according to claim 13, wherein the Drosophila promoter is inducible.

15. The method according to claim 13 wherein the first vector is pCOHYGRO.

16. The method according to claim 15, wherein the Drosophila promoter is the metallothionein promoter.

17. The method according to claim 15, wherein the Drosophila promoter is the Hsp-70 promoter.

18. The method according to claim 13, wherein the Drosophila promoter is constitutive.

19. The method according to claim 18, wherein the Drosophila promoter is the actin 5C promoter.

20. The method according to claim 18, wherein the Drosophila promoter is the 5'LTR of a COPIA element.

21. A gene expression unit comprising:

a DNA sequence selected from the group consisting of a sequence encoding HIV gp120 and a sequence encoding HIV gp160; and a regulatory element for transcription of said DNA sequence and translation within a Drosophila cell.

22. The gene expression unit of claim 21 wherein said regulatory element is selected from the group consisting of an actin 5C promoter and a Drosophila metallothionein promoter.

23. The gene expression unit of claim 22 comprising the HIV DNA coding sequence as present in pgp160Δ32, pgp120FΔ32, pgp120Δ32, or pgp120Δ274.

* * * * *